(12) United States Patent
Braun

(10) Patent No.: US 7,101,340 B1
(45) Date of Patent: Sep. 5, 2006

(54) SPECTROSCOPIC BREATH PROFILE ANALYSIS DEVICE AND USES THEREOF FOR FACILITATING DIAGNOSIS OF MEDICAL CONDITIONS

(76) Inventor: Charles L. Braun, 28 Hawk Pine Rd., Norwich, VT (US) 05055

( * ) Notice: Subject to any disclaimer, the term of this patent is extended or adjusted under 35 U.S.C. 154(b) by 0 days.

(21) Appl. No.: 10/411,887

(22) Filed: Apr. 11, 2003

Related U.S. Application Data

(60) Provisional application No. 60/372,295, filed on Apr. 12, 2002.

(51) Int. Cl.
*A61B 5/08* (2006.01)
*G01N 1/22* (2006.01)

(52) U.S. Cl. ............... 600/532; 73/23.3; 128/920; 128/923

(58) Field of Classification Search ........... 600/529, 600/538, 531–533; 128/920, 923–925, 203.12, 128/203.13; 73/23.3; 702/24; 422/84
See application file for complete search history.

(56) References Cited

U.S. PATENT DOCUMENTS

| 4,887,455 | A |   | 12/1989 | Payne et al. |  |
|---|---|---|---|---|---|
| 5,058,600 | A | * | 10/1991 | Schechter et al. | 600/529 |
| 5,303,575 | A |   | 4/1994 | Brown et al. |  |
| 6,067,989 | A | * | 5/2000 | Katzman | 128/898 |
| 6,248,078 | B1 | * | 6/2001 | Risby et al. | 600/529 |
| 6,254,547 | B1 |   | 7/2001 | Phillips |  |
| 6,428,483 | B1 | * | 8/2002 | Carlebach | 600/532 |
| 6,461,306 | B1 | * | 10/2002 | Hanson et al. | 600/532 |
| 6,540,691 | B1 |   | 4/2003 | Phillips |  |
| 6,609,068 | B1 | * | 8/2003 | Cranley et al. | 702/24 |
| 6,620,109 | B1 | * | 9/2003 | Hanson, III | 600/532 |
| 6,712,770 | B1 | * | 3/2004 | Lin et al. | 600/532 |
| 6,726,637 | B1 | * | 4/2004 | Phillips | 600/543 |
| 2001/0037070 | A1 |   | 11/2001 | Cranley et al. | 600/532 |
| 2002/0007249 | A1 |   | 1/2002 | Cranley et al. | 702/24 |
| 2002/0151814 | A1 | * | 10/2002 | Payne et al. | 600/532 |

FOREIGN PATENT DOCUMENTS

| WO |   | 2203553 | 10/1988 |
| WO | WO 03/049595 A2 | | 6/2003 |

OTHER PUBLICATIONS

Rizoli, Jay, Sensor Chip™: produced by Ion Optics sees the light with the optical gas sensors, The Journal of New England Technology, http://www.masshightech.com, pp. 1-3.
McCann, Patrick, Ph.D., Breathmeter™ by Ekips Technologies, ATS Journals, http://www.breathmeter.com., pp. 1-7.
Paldus, Barbara, Breath Gas Sensor for Improved Diagnosis and Patient Management for Diabetes and Asthma (LLNL-T2-0230-RU), Informed Diagnostics, Inc., www.infodiag.com, p. 1.

(Continued)

*Primary Examiner*—Robert L. Nasser
*Assistant Examiner*—Navin Natnilhithadha

(57) ABSTRACT

A medical diagnostic device for analyzing gases in expired breath. The device includes a spectroscopic analyzer component for obtaining a patient's breath concentration profile; a computer operably coupled to the analyzer component; a memory component operably coupled to the computer; and a database stored within the memory component containing spectroscopic breath analysis profiles. Each profile is characteristic of at least one of a plurality of medical conditions. A computer program compares the obtained patient's breath profile to the stored database of spectroscopic breath profiles, such that diagnosis of the presence or absence of a medical condition is facilitated.

45 Claims, 3 Drawing Sheets

A Schematic Diagram the CW- CRDS System

OTHER PUBLICATIONS

NEPHROLUX™ by Pranalytica, http://www.pranalytica.com/Nephrolux.him, pp. 1-5.

NEPHROLUX™: Breath Ammonia Analyzer.

Narasimhan, L.R. et al., Correlation of breath ammonia with blood urea nitrogen and creatinine during hemodialysis, Dept. of Physics and Astronomy, University of California, and Dept. of Nephrology, School of Medicine, University of California, Contributed by C. Kumar N. Patel, Feb. 5, 2001.

Rosenberg, Mel, The Science of Bad Breath, Scientific American, Apr. 2002, pp. 1-5.

Ahlberg, Erik, Breath Tests May Reveal Illnesses, The Wall Street Journal, Oct. 1, 2003.

Alving, K., et al., Increased-Amount of Nitric Oxide in Exhaled Air of Asthmatics, Eur. Respir. J., 1993, 6, pp. 1368-1370.

Amrani, M.E. Hassan, et al., An Intelligent Gas Sensing System, Sensors and Actuators B, 44 (1997) pp. 512-516.

Atherton, J.C., et al., The Urea Breath Test for Helicobacter Pylori, GUT, 1994, 35, pp. 723-725.

Bailey, R.T., et al, Thermal Lensing, Photoacoustic, Photothermal, and Photochemical Processes, Topics in Current Physics, ed. Hess, P. (Springer, Berlin), (1989) vol. 46, pp. 37-60).

Hatfield, J.V., et al., Towards an Integrated Electronic Nose using Conducting Polymer Sensors, Sensors and Actuators B, 18-19 (1994) pp. 221-228.

Jacoby, Mitch, Breath Analysis For Medical Diagnosis, C&EN Chicago, Mar. 29, 2004.

Narasimhan, L.R., et al., Correlation of Breath Ammonia with Blood Urea Nitrogen and Creatinine During Hemodialysis, PNAS, vol. 98, No. 8, pp. 4617-4621, Apr. 10, 2001.

O'Keefe, Anthony, et al., Cavity Ring-Down Optical Spectrometer for Absorption Measurements Using Pulsed Laser Sources, Rev. Sci. Instrum. 59 (12), pp. 2544-2551, Dec. 1988.

Paredi, Paolo, et al, Exhaled Carbon Monoxide Levels Elevated in Diabetes and Correlated with Glucose Concentration in Blood, CHEST, 116, 4, pp. 1007-1011, Oct. 1999.

Patel, C.K.N., Opto-Acoustic Spectroscopy Applied to the Detection of Gaseous Pollutants, Monitoring Toxic Substances, ACS Symposium Series, ed. Schuetzle, D., Am. Chem. Soc., Washington, DC, (1978), vol. 94, pp. 177-194.

Pauling, Linus, et al., Quantitative Analysis of Urine Vapor and Breath by Gas-Liquid Partition Chromatography, Proc. Nat. Acad. Sci. USA, vol. 68, No. 10, pp. 2374-2376, Oct. 1971.

Phillips, M., et al., Increased Pentane and Carbon Disulfide in the Breath of Patients with Schizophrenia, J. Clin. Pathol., 1993, 46, pp. 861-864.

Phillips, Michael, Breath Tests in Medicine, Scientific American, Jul. 1992.

Phillips, Michael, et al., Variation in Volatile Organic Compounds in the Breath of Normal Humans, Journal of Chromatography B, 729 (1999) pp. 75-88.

Phillips, M., et al., Volatile Organic Compounds in the Breath of Patients with Schizophrenia, Journal of Clinical Pathology, vol. 48(5), pp. 466-469, May 1995.

Romanini, D., et al., CW Cavity Ring Down Spectroscopy, Chemical Physics Letters 264 (1997) pp. 316-322.

Rosenberg, Mel, The Science of Bad Breath, Scientific American, vol. 286, issue 4, p. 72, Apr. 2002.

Scherer, J.J., et al., Cavity Ringdown Laser Absorption Spectroscopy: History, Development, and Application to Pulsed Molecular Beams, Chem. Rev. 1997, 97, pp. 25-51.

Stix, Gary, Breath Takers, Scientific American.com, Nov. 10, 2003 (http://www.sciam.com/print_version.cfm?articleID=0000D334-FF3E-1FAB-BF...).

Teranishi, Roy, et al., Gas Chromatography of Volatiles from Breath and Urine, Analytical Chemistry, vol. 44, No. 1, Jan. 1972.

* cited by examiner

A Schematic Diagram the CW-CRDS System

SPECTROSCOPIC BREATH PROFILE ANALYSIS DEVICE AND USES THEREOF FOR FACILITATING DIAGNOSIS OF MEDICAL CONDITIONS

The present application claims priority from U.S. Application No. 60/372,295, filed Apr. 12, 2002 which is incorporated herein by reference.

TECHNICAL FIELD

This invention relates generally to a medical device and protocols for using such a device to facilitate diagnosis of medical conditions in patients based on breath analysis profiles obtained using highly sensitive laser spectroscopies, for example Cavity Ring-down (CRD) spectroscopy, and photoacoustic (PA) spectroscopy. The relationship between gas concentration and ringdown time is given in many publications including D. Romanini, A. A. Kachanov, N. Sadeghi, F. Stoeckel, Chemical Physics Letters (1997) 264 316).

BACKGROUND

The potential for the use of exhaled breath as a diagnostic tool has long been recognized. Recently, researchers have shown that the chemical composition of expired breath can be an accurate, timely, and painless indicator of the health of an individual. See Phillips, M. et al., *J. Chromatography* (1999), B729, 75, hereby incorporated by reference herein. For example, a number of exhaled gases such as ammonia, nitric oxide, aldehydes and ketones have been associated with kidney and liver malfunction, asthma, diabetes, cancer, and ulcers. (Alving, K et al., *Eur. Respir. J.* (1993), 6, 1368; Paredi, P. et al., *Chest* (1999), 116, 1007; and Atherton, J., *Gut* (1994), 35, 723.) Other exhaled compounds like ethane, butane, pentane, and carbon disulfide have been connected to abnormal neurological conditions, including schizophrenia. (Phillips, M. et al., *J. Clin. Pathol.* (1993), 46, 861; and Phillips, M. et al., *J. Clin. Pathol.* (1995), 48, 466).

There is a relatively long history of using light absorption and emission by molecules as a means for qualitatively identifying which molecules are present in a mixture, and quantitatively determining what concentration of each is present. Commonly, molecules with two or more atoms show distinct absorptions in the infrared region of the spectrum, generally defined as light with a wavelength between 1 μm and 15 μm (11 μm=$10^{-6}$ m). The detailed characteristics of these "fingerprint" absorptions can be extremely sharp at low pressure for molecules that are in the gas phase, enabling both the qualitative and quantitative assays with very high selectivity.

A large number of industrial pollutant gases such as NO, $NO_2$, $NH_3$, $SO_2$, and $CH_4$ have also been readily detected using laser spectroscopy. Such gases are often detected in high concentrations at their sources and in very low concentrations in ambient atmosphere and stratosphere. One example is nitric oxide, found at very high concentrations in automobile emissions at the tailpipe, but detected at level of only ppm or less in the atmosphere. By characterizing the optical absorptivity of a sample of known concentration, the concentration of an unknown sample can then be determined. In order to facilitate such determinations, various techniques have emerged over the years allowing the accumulation of the required spectroscopic parameters for a wide variety of molecular gases. For example, development of conventional measurements of light throughput, calorimetry, cavity-ring down spectroscopy, (see O'Keefe, A. et al., *Rev. Sci. Instrum.* (1988) 59, 2544 and Scherer, J. J. et al., *Chem. Rev.* (1997), (Washington, D.C.) 97, 25.), and thermal distortion spectroscopy (see Bailey, R. T. et al., in *Photoacoustic, Photothermal, and Photochemical Processes, Topics in Current Physics*, ed. Hess, P. (Springer, Berlin), (1989) Vol. 46, pp. 37–60) have greatly aided such endeavors. In particular, ultra low-absorption measurements using calorimetric techniques, thus allowing sub-ppb detection of many gaseous components, have been shown to be widely applicable (see Patel, C. K. N. in *Monitoring Toxic Substances*, ACS Symposium Series, ed. Schuetzle, D. (Am. Chem. Soc., Washington, D.C.), (1978), Vol. 94, pp. 177–194).

Recently, Narasimhan et al. (*Proc. Natl. Acad. Sci. U.S.A.* (2001), 98, 4617, hereby incorporated by reference herein) showed that optoacoustic spectroscopic analysis of ammonia levels in patients with end-stage renal disease during hemodialysis could be correlated with blood urea nitrogen (BUN) and creatinine levels. Such a correlation allowed a means for assessment of nitrogenous waste loading in a patient's bloodstream in real time, as compared to a 24-hour (or more) delay for standard blood sample analysis for blood urea nitrogen and blood creatinine levels.

Many of these technologies are complex, expensive and difficult to calibrate. They have not been economically adapted for individual health care use. It has been suggested, however, that self-administered breath alcohol tests could be used (See, Brown et al. U.S. Pat. No. 5,303,575) by multiple individuals at bars or other locations where alcoholic beverages are served, to detect a predetermined level of breath alcohol.

There is also a product for analyzing bad breath on the market, a portable sulfide monitor, popular with dentists (see The Science of Bad Breath in *Scientific American*, April, 2002, p. 78).

SUMMARY OF THE INVENTION

In one particular embodiment of the invention there is provided a medical device for analyzing gases in expired breath for facilitating diagnosis of a medical condition, comprising: a spectroscopic analyzer component for obtaining a patient's breath concentration profile; a computer operably coupled to the analyzer component; a memory component operably coupled to the computer; a database stored within the memory component containing spectroscopic breath analysis profiles, each profile characteristic of at least one of a plurality of medical conditions; and a computer program for comparing the obtained patient's breath profile to the stored database of spectroscopic breath profiles, such that diagnosis of the presence or absence of a medical condition is facilitated.

In another embodiment a medical device for analyzing gases in expired breath for facilitating diagnosis of a medical condition utilizes a database of spectroscopic breath analysis profiles is stored within the memory component for medical conditions including kidney malfunction, liver malfunction, asthma, diabetes, cancer, ulcer, schizophrenia, neurological disorders, pneumonia, halitosis, alcohol ingestion, and organ trauma.

In another particular embodiment, a medical device for analyzing gases in expired breath for facilitating diagnosis of a medical condition is configured to analyze gases in expired breath such as ammonia, nitric oxide, ketones, methane, ethane, butane, pentane, carbon dioxide, carbon monoxide, oxygen, sulfur dioxide, carbon disulfide, hydrogen sulfide, methyl mercaptan, skatole, indole, cadaverine, putrescine, isovaleric acid, trimethylamine, and halogens and halogen compounds are analyzed.

Another particular embodiment includes a medical device for analyzing gases in expired breath for facilitating diagnosis of a medical condition with a spectroscopic analyzer component wherein the spectroscopic analyzer component is a laser spectrometer.

In yet another particular embodiment of the present invention there is provided a medical device for analyzing gases in expired breath for facilitating diagnosis of a medical condition with a spectroscopic analyzer component wherein the spectroscopic analyzer component is a cavity ring down spectrometer or other sensitive spectroscopic analyzer.

Another particular embodiment of the present invention is a medical device for analyzing gases in expired breath for facilitating diagnosis of a medical condition having a cavity ring down spectrometer wherein the spectroscopic analyzer component is a qualitative analyzer.

Still yet another embodiment of the present invention is a medical device for analyzing gases in expired breath for facilitating diagnosis of a medical condition having a cavity ring down spectrometer wherein the spectroscopic analyzer component is a quantitative analyzer.

Another embodiment of the present invention is a method for using a medical device for analyzing gases in expired breath for facilitating diagnosis of a medical condition with a spectroscopic analyzer component to analyze a patient's breath sample for facilitating diagnosis of the presence or absence of a medical condition, comprising: obtaining a breath sample from a patient; analyzing volatile components of the patient sample to provide a patient spectroscopic breath profile; comparing the patient's spectroscopic breath profile to a database of spectroscopic breath profiles, each database profile characteristic of at least one of a plurality of medical conditions, so as to facilitate diagnosis of the presence or absence of a medical condition.

An additional particular embodiment of the present invention is a method for using a medical device for analyzing gases in expired breath for facilitating diagnosis of a medical condition with a spectroscopic analyzer component having a spectroscopic analyzer that is a cavity ring down spectrometer to analyze a patient's breath sample for facilitating diagnosis of the presence or absence of a medical condition, comprising: obtaining a breath sample from a patient; analyzing volatile components of the patient sample to provide a patient spectroscopic breath profile; comparing the patient's spectroscopic breath profile to a database of spectroscopic breath profiles, each database profile characteristic of at least one of a plurality of medical conditions, so as to facilitate diagnosis of the presence or absence of a medical condition.

Yet another particular embodiment of the present invention is a method as described above for using a medical device in accordance with a medical device for analyzing gases in expired breath for facilitating diagnosis of a medical condition with a spectroscopic analyzer component having a spectroscopic analyzer that is a cavity ring down spectrometer wherein the method comprises obtaining a breath sample from a patient; analyzing volatile components of the patient sample to provide a patient spectroscopic breath profile; comparing the patient's spectroscopic breath profile to a database of spectroscopic breath profiles, each database profile characteristic of at least one of a plurality of medical conditions, so as to facilitate diagnosis of the presence or absence of a medical condition, wherein the analyzing step further comprises a qualitative analysis.

And still another particular embodiment of the present invention is a method for using a medical device for analyzing gases in expired breath for facilitating diagnosis of a medical condition with a spectroscopic analyzer component having a spectroscopic analyzer that is a cavity ring down spectrometer wherein the method comprises obtaining a breath sample from a patient; analyzing volatile components of the patient sample to provide a patient spectroscopic breath profile; comparing the patient's spectroscopic breath profile to a database of spectroscopic breath profiles, each database profile characteristic of at least one of a plurality of medical conditions, so as to facilitate diagnosis of the presence or absence of a medical condition, wherein the analyzing step further comprises a quantitative analysis.

BRIEF DESCRIPTION OF DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
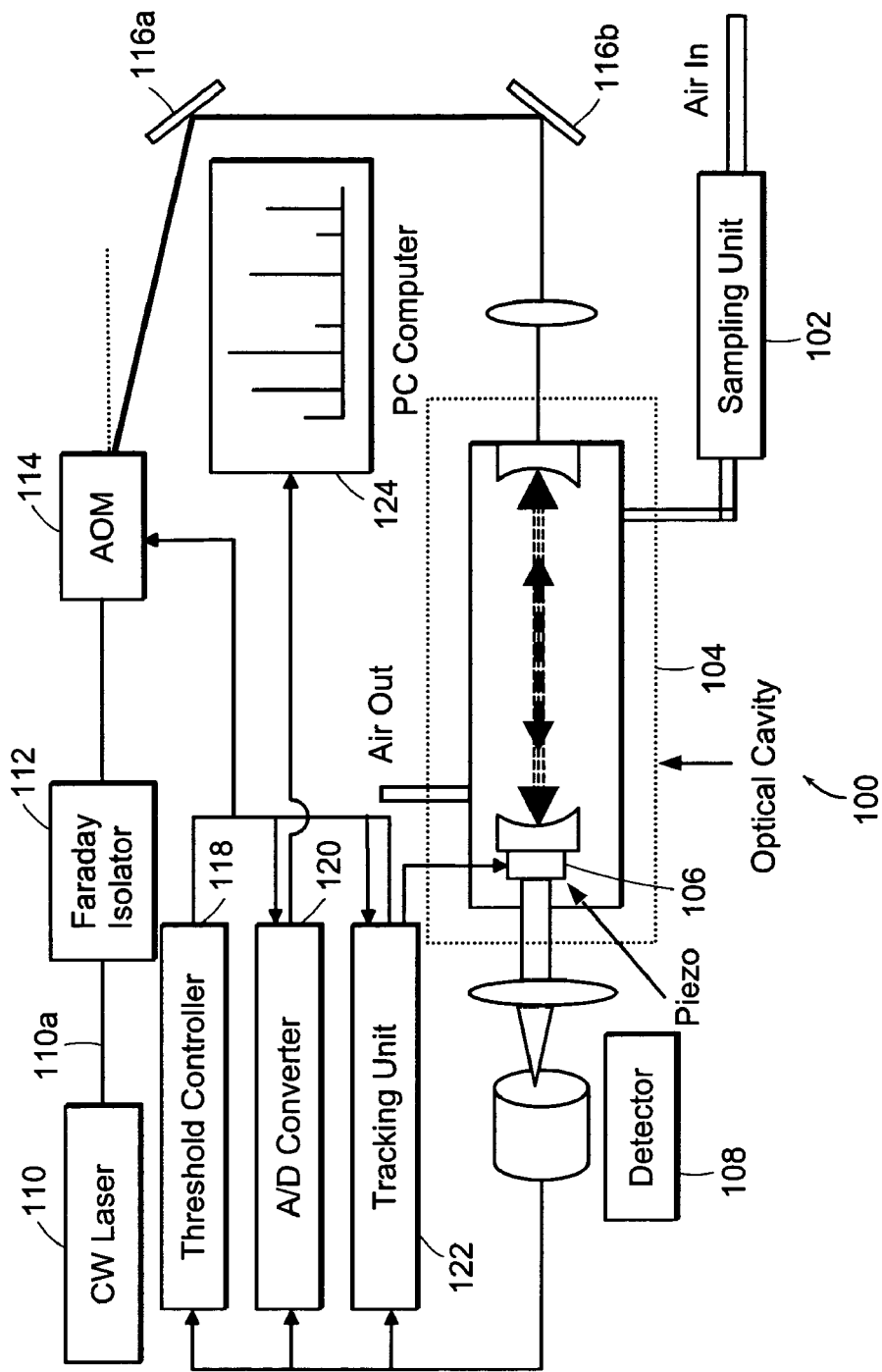
FIG. 1 is a schematic representation of an embodiment of the present invention.

Analysis of breath samples for diagnostic purposes has the advantage that the breath sample to be analyzed is collected from the patient in a non-invasive manner with a minimum of discomfort or inconvenience. The basic components of the analyzer component 100 of one device in accordance with the present invention can be further understood with reference to FIG. 1. FIG. 1 illustrates a schematic diagram of a spectroscopic analyzer component of one embodiment of the present invention wherein the spectroscopic analyzer is a cavity ring down spectrometer.

A patient initially exhales into a sampling unit 102 which captures the exhaled breath. The exhaled breath sample is then directed to an optical cavity 104 containing a piezo 106 coupled to a detector 108. At least one CW laser 110 generates at least one laser light beam 110a which is directed through a Faraday isolator 112 and an acousto-optic modulator (AOM) 114. The laser light beam is then focused using one or more mirrors such as 116a and 116b and passed through the optical cavity 104 containing the exhaled breath sample. A threshold controller 118, operably coupled to an A/D converter 120 and a tracking unit 122, is in communication with detector 108 and AOM 114, and is further interfaced with a computer 124.

The data resulting from the analysis could then be transferred to and stored in computer 124, which may further have an input device or devices, such as a keyboard or mouse, an output device such as a video monitor, printer, or other means of displaying data, memory, and an appropriate CPU. The computer may also be connected to an information grid such as a telephone system or the Internet.

System 100 should be calibrated as required, which may be done by injecting a gas of known composition into the sampling device. A gas-filled canister may be provided for this purpose. It is also important to purge the sampling device after use to discharge excess moisture or other components. Purging could be done, for example, by injecting the sampling device with dry nitrogen. In such a system, the two functions of calibration and purging may thereby be performed in a single step. Alternatively, the calibration gas and the purging gas may be different, and the two functions performed in separate steps. Certain types of analyzers are more stable and require less calibration than others. Cavity ring-down spectroscopy, for example, may require reference or "zero" calibration, but will otherwise remain stable unless the associated laser or cavity is changed.

Sampling Modes

Sampling is any means of bringing exhaled breath into sampling unit 102. In one particular embodiment, sampling unit 102 is a spectrometer cell. Prior to sampling, sampling unit 102 is standardized for use. In one embodiment in accordance with the present invention, standardization consists of flushing sampling unit 102 with dry nitrogen gas, which has substantially no absorption of near-IR light (800–2000 nm). Ringdown (rd) time, $\tau_0$, at the wavelength to be used for detection of the analyte, is a maximum determined chiefly by the reflectivity of sampling unit mirrors. Prior to analysis for each new analyte, sampling unit 102 is standardized at the wavelength to be used for the new gas (analyte). After use, dry nitrogen gas is isolated in sampling unit 102 by valves.

Static Sample

For this sampling mode, no flow occurs during measurements and the sample is isolated by valves. Alternatively, the subject just quits blowing during the measurement. For example, the subject establishes a steady breathing cycle of shallow, normal, or deep breaths, as instructed. Once the cycle is established, the subject exhales into a disposable mouthpiece connected to a standard respirometer tube which is connected to sampling unit 102 with intervening filters for particulates and moisture. A check valve insures that flow is unidirectional from the subject into the sampling unit. If needed, multiple exhalations are used to completely purge sampling unit 102 and fill it uniformly with the subject's breath.

In such a sampling mode, sampling unit 102 is isolated during measurement using solenoid valves. The procedure is repeated as needed to obtain meaningful concentrations of the analytes being measured.

Continuous Sampling

Figure 2A:
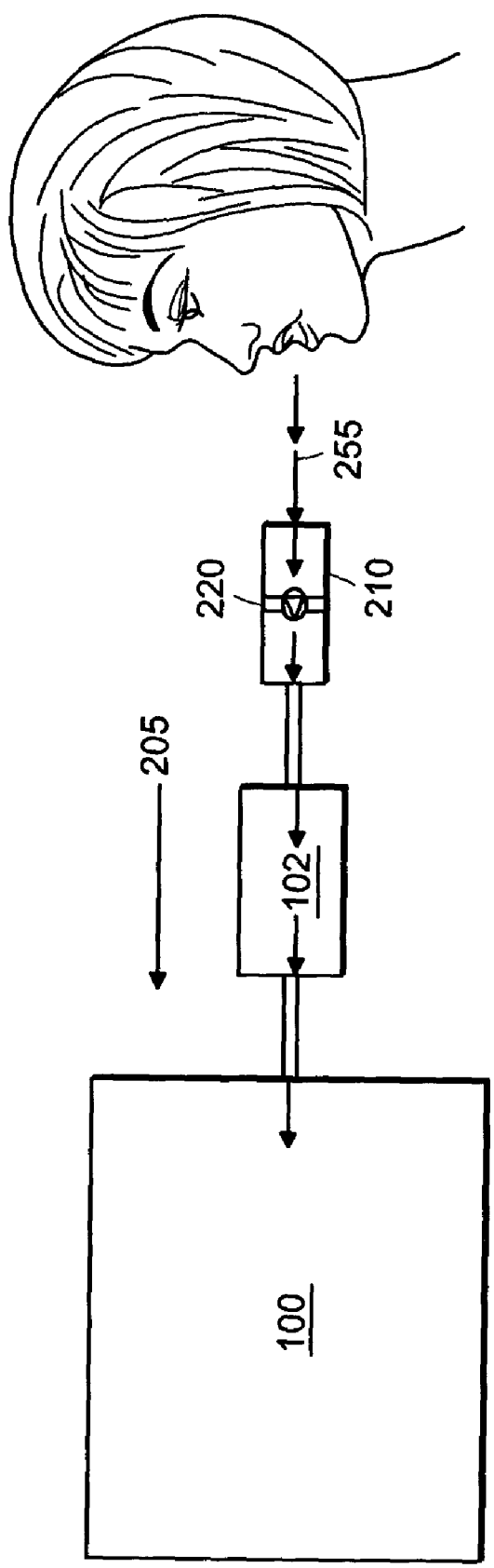
FIG. 2A is a schematic showing an embodiment of how an episodic sampling mode may be implemented.
Figure 2B:
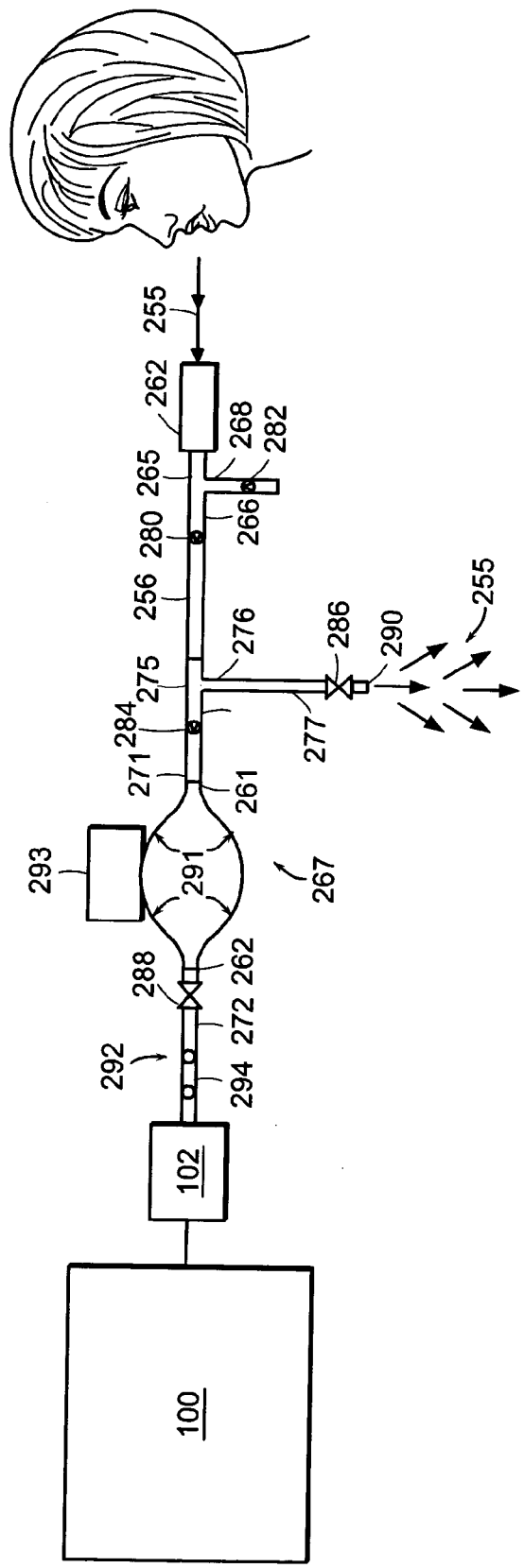
FIG. 2B is a schematic showing an embodiment of how a steady state sampling mode may be implemented.

There are two continuous sampling measurement modes: episodic and steady state. Each requires that the spectrometer be tuned to the wavelength of interest depending on the analyte (gas) to be measured.

a. Episodic sampling:

In this mode, as depicted in FIG. 2A, a subject exhales normally into a respirometer tube 210 and inhales through the nose. A check valve 220 permits flow 205 only in the direction of exhalation so that no freshly exhaled breath is inhaled. As the subject breathes, the flow 205 of exhaled breath 255 through sampling unit 102 varies with time. Variations over time in the concentration of the gas of interest may be independent of variations over time in flow 205 of exhaled breath 255. In this sampling mode, once a reproducible record is obtained and recorded by the computer, the procedure is complete.

b. Steady State Sampling:

In this sampling mode, as depicted in FIG. 2B, a small portion (ca. 10%) of a subject's exhaled breath 255 is continuously sampled through sampling unit 102 at a substantially constant flow. Constant flow is provided from a bag reservoir 267 that the subject continuously fills by exhaling into a respirometer mouthpiece 262 connected at outlet 264 to a first "Y" fitting 265. A right outlet 266 of the first "Y" fitting 265 feeds a first check valve 280 connected to exhaled breath tube 256. First check valve 280 serves to prohibit reverse flow from exhaled breath tube 256 back into the subject. A left outlet 268 of first "Y" fitting 265 has a second check valve 282, disposed in opposite flow direction from that of first check valve 280 that closes on exhalation and opens on inhalation to allow mouth breathing by the subject.

On exiting first check valve 280, exhaled breath 255 flows into a tube 256 that feeds a second "Y" fitting 275. A left outlet 276 of a second "Y" fitting 275 feeds a tube 277 that exhausts to atmosphere, and a right outlet 278 of second "Y" fitting 275 feeds a third check valve 284 connected via a tube 271 to bag inlet 261. The amount of breath 255 exhausted to the atmosphere is controlled by an adjustable flow proportioning valve 286 at the site of exhaust 290.

The balance of breath 255 flows through third check valve 284 and into bag reservoir 267. Bag reservoir 267 is held at constant selected pressure 291, for example, by using a predetermined and pre-selected weight 293 on the top of bag reservoir 267.

Third check valve 284 before bag reservoir inlet 261 prohibits reverse flow to exhaust 290 during subject inhalation. Bag reservoir outlet 262 feeds a tube 272 connected to a flow control valve 288 for adjusting the amount of exhaled breath 255 conducted to sampling unit 102 and further through particulate and moisture filters 292 and 294.

Alternatively, filters 292 and 294 may also be positioned at bag inlet 261 to eliminate condensation in bag reservoir 267 which may have adverse consequences due to adsorption of the analyte in the condensed moisture on the walls of the bag.

In accordance with another embodiment of the present invention, the spectroscopic analyzer component includes an optoacoustic analyzer, such as the system depicted in Figure 1 of Narasimhan et al., PNAS 98, 4617 at 4618 (2001), the entire contents of which have been incorporated by reference (vide supra).

The entire sample, or a portion thereof, is processed quantitatively or qualitatively. Quantitative analyzers may include highly sensitive laser spectroscopic devices such as cavity ring down spectrometers, and optoacoustic spectrometers described above. Such devices may also be used qualitatively, to test for the mere presence of an exhaled gas. Optionally, a second analyzer is provided that is used for qualitative analysis. Exemplary analyzers include ion mobility spectrometer detectors, acoustic wave detectors, and fiber optic detectors. Processed data from both the quantitative analyzer and/or the qualitative analyzer are stored in the memory of the computer and compared to a database of spectroscopic breath profiles characteristic of one or more medical conditions. Preferably both quantitative and qualitative analyses is performed using the same laser spectroscopy analyzer.

In accordance with embodiments of the present invention, data from a particular patient are stored so that multiple samples over an extended period of time may be taken. This permits a baseline to be established for a particular patient, and trend analysis is performed on the resulting data, relative to the database of spectroscopic breath profiles. If there is an acute and significant change in the chronic condition of the patient's breath, indications of this change may be communicated to a physician or healthcare provider via communications components linked to the computer 124.

The types of tests that may be employed include carbon dioxide content, alcohol content, lipid degradation products, aromatic compounds, thio compounds, ammonia and amines or halogenated compounds. As an example of the usefulness of detecting these components, lipid degradation products such as breath acetone are useful in monitoring diabetes. Thio compounds such as methanethiol, ethanethiol, or dimethyl sulfides have diagnostic significance in detecting widely differing conditions, such as psoriasis and ovulation. Increased ammonia has been associated with hepatic disease. Halogenated compounds may be indicative of environmental or industrial pollutants.

Another set of tests is based on analysis of certain breath components after the patient has taken a diagnostic reagent, in accordance with instructions from a physician. For example, urea, especially $C^{13}$-labeled urea, or $C^{13}$-labeled carbohydrates may be taken orally and the $C^{13}$-based $CO_2$ metabolite analyzed in the exhaled breath to determine if the patient has heliobactor pylori infection of the stomach lining (urea $NH_3+CO_2$) or carbohydrate malasorbtion, glucose intolerance, lactase deficiency or small bowel bacterial overgrowth. Carbon 13 isotopes can be differentiated by laser spectroscopy.

A baseline or chronic breath condition history for a particular patient may also be compiled using the present invention. In this embodiment, an initialization test is first run on a sample of the patient's exhaled breath, with additional samples analyzed thereafter. As additional samples are analyzed and stored in memory at specific times over an extended period of time, the last stored or baseline sample data is then recalled from memory and the change or delta information between the new sample data and stored sample data is determined. Multiple analyses may be done simultaneously or serially on a single sample if the analyzer device 100 is capable of multiple analyses. Otherwise, an additional sample or samples may be requested of the patient. Cavity-ring-down spectroscopy, for example, is capable of measuring multiple components in a short period of time.

If qualitative tests are to be performed, the tests may fall into two general types. First, the presence of the breath component alone may be significant to the health of the patient. This is particularly important where the chronic monitoring of the breath components of the patient indicate the absence of a component and that component appears in a new breath sample analysis. The converse change may also be significant, that is, a component formerly present is absent in the new breath sample analysis. Both conditions may be detected by a device in accordance with the present invention if maintenance of a patient's specific data history is desired and preserved in memory.

Second, it may be significant that a newly detected component falls within a given range. Although the components may be detected by a qualitative analysis, estimates of the range may be obtained by certain manipulations of the qualitative device. This is important where it is economically infeasible to employ a quantitative device with respect to a particular component, but where an approximation can be obtained which is sufficient to alert an attending physician of the need for a more detailed analysis, or which is sufficient to allow the patient to follow a course of treatment, e.g. diet control, either for weight loss or for diabetes.

After the qualitative components are identified, it may be desirable to quantify certain of those components. If a quantitative approximation is desired, a desired range is determined by first establishing a limit for the particular component to be analyzed. This involves setting the level of detection LOD to a particular level such that the component is longer detected because the minimum level is below the "pre-set" detection limit of the detector. If the desired component in the breath sample is not detected, this indicates that the component is below a selected maximum. If necessary, a new sample is taken and then a determination made for whether the component is present at that level of detection LOD. If the component is not detected, it is reported that the component falls below the selected limit. On the other hand, if the component is detected, it is reported that the component's concentration exceeds the selected limit. The data is then stored, indicating that the particular component meets or does not meet the selected minimum detection level. This may be sufficient to determine if the component is low enough for health or if it exceeds a healthy range.

If it is desired to place the component within a maximum and minimum range, a test for a second limit is performed. For the second limit, the upper limit, a new setting for the LOD is provided and the cycle is repeated at the second selected setting, as described.

The results obtained from the quantitative analyses, the minimum detection analyses, and the minimum/maximum range analyses are then examined by computer 124. Depending on the desired information, computer 124 checks for significant changes in the quantitative or qualitative analyses for selected components, whether over time for a particular patient as compared to a database of spectroscopic profiles characteristic of a plurality of medical conditions, or as a single analysis compared to the database of spectroscopic breath profiles. Significant deviations over time from the database profiles, or a significant deviation as a single analysis are then used by a health care professional to facilitate diagnosis of the presence/absence and/or progression/regression of a medical condition.

The use of the breath analyzer 100 is further explained as follows. Use of the breath analyzer 100 begins with calibration. This is accomplished by injecting a gas of known composition into the device. A canister of such gas is provided for this purpose. After calibration, a sample is taken. The analyzer 100 then compares the spectroscopic breath profile for a patient to a database of spectroscopic profiles characteristic of one or more medical conditions to facilitate diagnosis for the presence or absence of a medical condition. Computer 124 alerts the user to a "match" or "nonmatch" in patient versus database spectroscopic profiles. Such information is then interpreted by a physician or other health care professional to facilitate diagnosis of the presence or absence of a medical condition. The "match/nonmatch" information may be stored in the memory of the medical device, to be retrieved and/or transferred as required.

The analyzer may also request the user or patient to enter certain data through the microcomputer user interface (for example, keyboard or mouse). The requested data might include diet information, perceived general state of health, amount and duration of recent exercise and similar factors which might either explain an acute change in breath components (that is, indicate that the change is not in fact significant) or provide important information for a health care provider.

Finally, the system is purged to prevent contaminants from building up in the sampling device. This may be accomplished by providing a gas of known composition such as pure dry nitrogen, and may be combined with the calibration step.

Multiple tests performed on a single sample may be independent, or may be the results of several tests combined to produce a template or pattern representative of a patient's condition or representative of the presence of a particular compound or set of compounds. Multiple lasers may also be used on a single sample to extend the band width for detection, and pattern recognition may then be applied to the combined output of the several lasers. A single laser is generally capable of emitting light at certain limited frequencies. Although some tuning or variation of frequencies is possible, the elements or compounds that can be effectively recognized by a single laser device are limited by the frequency characteristics of the selected laser. The detector 108 of an embodiment of the present invention may include multiple lasers having different emission frequencies. The lasers may be directed into a single sample by being physically offset around the sample, by being fired at slightly different times, or may be directed by other techniques. Optical apparatus such as mirrors, lenses or prisms may be used to direct a beam from a selected laser along a path through the sample and into a detector. By adjusting the optical apparatus, beams from other lasers may be directed along the same or a similar path through the sample. By using lasers with different emission characteristics with the same sample, a wider set of data points may be obtained. Instead of three or four data points for a single laser, three lasers may obtain twelve or more data points from the same sample. This information is expected to be both more selective and more quantitatively precise than similar information obtained by electronic nose technology. The resulting more accurate information from all the laser beams is nevertheless processed together, using pattern recognition methods and techniques. As a result, a wider range of conditions or compounds is identified by correlating the data pattern or changes in the data pattern over time.

The described examples of particular embodiments of the present invention are by means of illustration and should not be considered limiting. Persons skilled in the art will readily recognize possible changes and modifications to be incorporated into the design or construction that would not depart from the spirit and scope or teachings of the presently claimed invention.

What is claimed is:

1. A medical device for analyzing gases in a person's expired breath for assisting in diagnosis of a medical condition, which device comprises:
   a spectroscopic analyzer component that obtains a patient's breath profile that includes at least molecular identification of at least a plurality of compounds that are present in the patient's breath;
   a computer;
   a memory component operably coupled to the computer; and
   a database stored within the memory component containing spectroscopic breath analysis profiles, each profile characteristic of at least one of a plurality of medical conditions; wherein
   the computer is operably coupled to the analyzer component and compares the obtained patient's breath profile, including the identified molecular compounds, to the stored database of spectroscopic breath profiles to provide information pertinent to diagnosis of the presence or absence of a medical condition.

2. A medical device according to claim 1 wherein the database of spectroscopic breath analysis profiles stored within the memory includes profiles for medical conditions including kidney malfunction, liver malfunction, asthma, diabetes, cancer, ulcer, schizophrenia, neurological disorders, pneumonia, halitosis, alcohol ingestion, and organ trauma.

3. A medical device according to claim 1 wherein the spectroscopic analyzer identifies molecular compounds in expired breath, which compounds include ammonia, nitric oxide, ketones, methane, ethane, butane, pentane, carbon dioxide, carbon monoxide, oxygen, sulfur dioxide, carbon disulfide, hydrogen sulfide, methyl mercaptan, skatole, indole, cadaverine, putrescine, isovaleric acid, trimethylamine, and halogens, and halogen compounds.

4. The medical device according to claim 1 wherein the spectroscopic analyzer component is a highly sensitive laser spectrometer.

5. The medical device according to claim 4 wherein the spectroscopic analyzer component is a cavity ring down spectrometer.

6. The medical device according to claim 4 wherein the spectroscopic analyzer component is an optoacoustic spectrometer.

7. A method for using the medical device of claim 4 to analyze a patient's breath sample for assisting in diagnosis of the presence or absence of a medical condition, comprising:
   obtaining a breath sample from a patient;
   analyzing volatile components of the patient sample to provide a patient spectroscopic breath profile that includes both qualitative and quantitative data;
   comparing the patient's spectroscopic breath profile to a database of spectroscopic breath profiles, each database profile characteristic of at least one of a plurality of medical conditions, so as to provide information pertinent to diagnosis of the presence or absence of a medical condition.

8. The medical device according to claim 1 wherein the spectroscopic analyzer component also is a quantitative analyzer.

9. The medical device according to claim 1 wherein the database is capable of storing data from multiple spectroscopic analyses over an extended time period.

10. A method for using the medical device of claim 1 to analyze a patient's breath sample for assisting in diagnosing the presence or absence of a medical condition, comprising:
    obtaining a breath sample from a patient;
    analyzing volatile components of the patient sample to provide a patient spectroscopic breath profile that includes both qualitative and quantitative data;
    comparing the patient's spectroscopic breath profile to a database of spectroscopic breath profiles, each database profile characteristic of at least one of a plurality of medical conditions, so as to provide information pertinent to tie presence or absence of a medical condition.

11. The medical device of claim 9, wherein the computer is capable of establishing a baseline for a particular patient and is capable of noticing a change from the baseline.

12. The medical device of claim 1, wherein the computer is capable of providing information that alerts a user of the computer of a significant deviation from previous spectroscopic breath profiles.

13. A method of analyzing gases from the breath of a patient in diagnosing a medical condition in that patient, which method comprises:
    (a) sampling a patient's breath;
    (b) spectroscopically analyzing volatile components of the sample to provide a patient spectroscopic breath profile that includes at least qualitative molecular identification of compounds or a combination of both qualitative and quantitative molecular identification of compounds; and (c) comparing the patient's spectroscopic breath profile to a database of spectroscopic breath profiles through use of a computer, wherein each profile in the database is characteristic of at least one of a plurality of medical conditions, to provide information pertinent to a diagnosis of the presence or absence of a medical condition.

14. The method of claim 13, wherein the computer provides information to a user thereof of a match or non-match of the patient's spectroscopic breath profile to at least one of the profiles in the database.

15. The method of claim 14, wherein the information is interpreted by a health care professional to evaluate the presence or absence of a medical condition.

16. The method of claim 15, further comprising entering additional information into the computer regarding the patient.

17. The method of claim 13, wherein the spectroscopic analysis provides a spectroscopic breath concentration profile.

18. The method of claim 13, wherein the spectroscopic breath profile includes both qualitative and quantitative data.

19. A device to assist in diagnosing a medical condition, which device comprises:

(a) a spectroscopic analyzer component that obtains first information regarding qualitative identification, or a combination of both qualitative and quantitative identification, of molecules present in a sample of a patient's breath; and (b) a computer that receives the first information regarding qualitative or qualitative and quantitative molecular identification and that compares the first information with second information in a database, wherein the second information comprises data concerning molecules present in human breath and certain medical conditions, and wherein the comparison results in the computer providing third information to the patient or a health care professional.

20. The device of claim 19, wherein the computer program also is capable of storing data from multiple breath samples of the patient, taken over an extended time period.

21. The device of claim 19, wherein the computer is further capable of providing a baseline of data from one of more samples of the patient's breath.

22. The device of claim 20, wherein the computer is capable of providing a trend analysis with respect to receiving multiple inputs of the first information.

23. The device of claim 20, wherein when providing the third information, the computer is capable of alerting the patient or health care professional of significant deviations in the first information.

24. The device of claim 23, wherein the computer is further capable of alerting the health care professional of the need for further analysis or for a proposed course of treatment.

25. The device of claim 19, wherein the spectroscopic analyzer component obtains first information regarding both qualitative and quantitative identification of molecules present in a sample of the patient's breath.

26. A method suitable for use in diagnosing the presence or absence of a medical condition in a patient, which method comprises:

(a) spectroscopically analyzing a sample of a patient's breath to obtain first information that includes at least qualitative identification of molecules that are present in the sample;

(b) comparing the first information, including the qualitative molecular identification, to second information through use of a computer, the second information comprising data concerning molecules present in human breath and the relationship of those molecules to certain medical conditions; and (c) providing third information, which third information includes results of the comparison, to a health care professional through use of the computer to assist the health care professional in evaluating a presence or absence of the medical condition.

27. The method of claim 26, wherein the comparison of the first information to the second information through use of the computer includes a comparison of both the qualitative and quantitative molecular identification of the first information to qualitative and quantitative data of the second information.

28. The method of claim 27, further comprising storing the first information so that it can be compared to subsequent submissions of the first information for purposes of assisting in the diagnosis of the patient.

29. The method of claim 26, wherein multiple samples of first information are stored so that a baseline is established for the patient.

30. The method of claim 29, wherein difference between the baseline and the first information can be detected and wherein the third information can alert the health care professional that the differences have been detected.

31. The method of claim 26, wherein the spectroscopic analysis involves the detection of carbon dioxide content, alcohol content, acetone content, lipid content aromatic compound content, thio compound content, ammonia content, amine content halogen content, and combinations thereof; and wherein the first information includes results of the detection of such content.

32. The method of claim 26, further comprising:

(d) providing the patient with a diagnostic reagent prior to obtaining a sample of the patient's breath and spectroscopically analyzing the particular sample.

33. The method of claim 26, wherein the comparison may detect the presence or absence of a particular molecular component and/or notice whether the particular molecular component has a different quantitative presence when compared to prior submissions of first information or when compared to second information.

34. The method of claim 26, wherein the comparison can determine whether a particular molecular component meets a selected minimum detection level.

35. The method of claim 26, wherein the comparison can note significant deviation(s) from various inputs of first information, and wherein the provision of third information can notify the health care professional of the deviation(s).

36. The method of claim 26, wherein the comparison can detect a match or non-match of qualitative and quantitative identification of molecules in the first information with spectroscopic profiles of the second information.

37. The method of claim 36, wherein the match or non-match information can be stored in the computer.

38. The method of claim 26, further comprising entering additional information into the computer regarding the patient.

39. The method of claim 38, wherein the additional information includes diet information, general state of health, amount and/or duration of recent exercise, or combinations thereof.

40. The method of claim 26, wherein multiple lasers are used to perform the spectroscopic analysis.

41. The method of claim 40, wherein the multiple lasers have different emission frequencies.

42. A method suitable for use in diagnosing the presence or absence of a medical condition in a patient, which method comprises:
(a) comparing first information from a spectroscopic analysis of a sample of a patient's breath, which first information includes at least qualitative identification of molecules present in the spectroscopically analyzed sample, to second information through use of a computer, wherein the second information comprises information concerning molecules present in human breath; and
(b) providing third information, which third information includes results of the comparison, to a patient or health care professional(s), the information being provided at least in part through use of the computer and being helpful in assisting the patient or health care professional(s) in evaluating a presence or absence of a medical condition.

43. The method of claim 42, wherein multiple comparisons of multiple spectroscopic analyses from multiple samples of the patient's breath are performed.

44. The method of claim 42, wherein the comparison is made between the first information that includes both quantitative and qualitative identification of molecules present in the sample of the patient's breath and the second information that includes both qualitative and quantitative information regarding molecules present in human breath.

45. The method of claim 44, wherein the comparison of the first information to the second information is made with the second information also including information regarding human breath profiles and their relationships to certain medical conditions.

* * * * *